United States Patent [19]

Son et al.

[11] Patent Number: 5,071,981

[45] Date of Patent: Dec. 10, 1991

[54] ALKYLATED OXO-PIPERANZINYL-TRIAZINE

[75] Inventors: Pyong-Nae Son, Akron; John T. Lai, Broadview Heights; Peter D. Smith, Strongville, all of Ohio; Leonard E. R. Kosinski, Washington, W. Va.

[73] Assignees: The B. F. Goodrich Company, Akron, Ohio; E. I. du Pont de Nemours and Company, Wilmington, Del.

[21] Appl. No.: 495,658

[22] Filed: Mar. 19, 1990

[51] Int. Cl.$^5$ .......................................... C07D 403/12
[52] U.S. Cl. ...................................................... 544/198
[58] Field of Search ......................................... 544/198

[56] References Cited

U.S. PATENT DOCUMENTS

| | | | |
|---|---|---|---|
| 4,190,571 | 2/1980 | Lai et al. | 260/45.8 N |
| 4,292,240 | 9/1981 | Lai et al. | 260/239.3 R |
| 4,298,737 | 11/1981 | Lai et al. | 544/360 |
| 4,480,092 | 10/1984 | Lai et al. | 544/113 |
| 4,816,507 | 3/1989 | Cantatore et al. | 524/100 |

FOREIGN PATENT DOCUMENTS 63-86711 4/1988 Japan .

*Primary Examiner*—John M. Ford
*Attorney, Agent, or Firm*—Alfred D. Lobo

[57] ABSTRACT

A stabilizer compound for synthetic resinous materials is a tri-substituted triazine in which each substituent is a $N^4$-methylated 2-keto-1,4-diazacyclohexane connected to the triazine ring through an alkylene bridge. This bridge permits efficient methylation of the $N^4$ atom in every substituent under conditions which yield crystals having at least 90% purity. These crystals may be further purified to at least 95% purity at which purity level they contain less than 500 ppm ash. The stabilization effect of 95% pure compound in a polyacetal is such that, even with an ash content of 50 ppm, it has better stabilization properties than its 99.2% pure precursor (the non-methylated tri-substituted triazine) with an ash content of 10 ppm, as evidenced by lower formaldehyde evolved and better color retention, that is, developing less color in a water white sample after testing at 259° C.

3 Claims, No Drawings

ALKYLATED OXO-PIPERANZINYL-TRIAZINE

BACKGROUND OF THE INVENTION

This invention relates to an alkylated (i.e., $C_1$–$C_3$) derivative of a known compound and a method for producing it. The known compound is an oxo-piperazinyl triazine ("PIP-T" for brevity) which consists of a triazine ring having three polysubstituted piperazine-2-one ("PSP") substituents, each distally spaced apart from each C atom of the triazine ring by a polyalkyleneamine bridge. The PSP substituent is so termed because the 3- and 5- C atoms of the diazacyclohexane ring are each disubstituted with methyl groups.

As will immediately be apparent, a PIP-T is a large molecule. It is known that when this molecule is present in an organic material in an amount sufficient for the purpose at hand, there results a thermooxidatively stabilized composition, resistant to degradation by UV light. The general structure of a PIP-T is disclosed in U.S. Pat. No. 4,480,092 to Lai, et al. (class 544/subclass 113), the disclosure of which is incorporated by reference thereto as if fully set forth herein. PSP compounds are taught in U.S. Pat. Nos. 4,190,571; 4,292,240; and 4,298,737 inter alia. Like PIP-Ts, the 3,3,5,5-tetra-substituted PSPs provide excellent light stabilization, but have substantially lower thermooxidative stabilization than PIP-Ts.

As one skilled in the art will readily appreciate, the stabilization properties of both PSPs and PIP-Ts are attributable to the hindered $N^4$ atom in each PSP, steric hindrance being the result of having di-substituted 3- and 5- C atoms. The superior overall stabilization properties of a PIP-T substituted with three 3,3,5-5-tetraalkyl-substituted PSPs is attributable to the triazine ring and the bulky configuration of this specific PIP-T of this invention. All references to PSPs hereafter are to the 3,3,5-5-tetraalkyl-substituted piperazinone moieties; and reference to "the PIP-T" refers to a triazine ring substituted with three such PSPs, each distally spaced apart from the triazine ring by an ethyleneamine bridge and connected to the ring by a tertiary N atom.

To the extent that bulk contributed to stabilization, the obvious way to increase the overall bulk of the PIP-T is to provide bulky substituents at the 3- and 5- positions of the PSP ring, and at the N atom in the ethyleneamine bridge of an '092 PIP-T. Though this bridge on each of the three PSPs connected to the triazine ring adds to the bulk of the molecule, each bridge provides its connected PSP with requisite mobility sufficient to permit alkylation of the hindered $N^4$ atom with a methyl group, an ethyl group, or a propyl group. Still other suggested substituents are those at the 6-position of the diazacyclohexane ring and the $N^4$ position, which substituents are suggested by Conetta, et al. in U.S. Pat. No. 4,753,979. There was no particular reason for anyone to provide any substituent at the $N^4$ atom of the PSP, and any inclination to do so would be dispelled by the knowledge that the steric hindrance at the $N^4$ atom militated against making such a substitution.

Therefore there was no motivation to make any substitution at the $N^4$ atom. It was not foreseeable that a PIP-T that was alkylated with a methyl group, ethyl group, or propyl group, preferably with a methyl group, would have a unique and distinctive stabilization effect on the susceptibility of specific synthetic resinous materials, quite different from the effect obtained by the known unmethylated compound, itself an excellent stabilizer.

Having successfully alkylated the $N^4$ atom specifically with a methyl group, it was discovered quite fortuitously, that the methyl substituent in the PIP-T (hence "methylated PIP-T") was unexpectedly effective as a stabilizer for polyacetal resins. Since providing a methyl (or ethyl or propyl) substituent on the ring N atom of a diazacyclohexane is typically a routine task, this would appear to present little difficulty. However, the methylation (or ethylation or propylation) must be successful on each hindered $N^4$ atom of each of the three PSPs, yet not occur at any other location in the PIP-T. It was not apparent how this could be done.

Moreover, as will readily be appreciated, the stabilization effect sought will only be realized if a mass of essentially pure methylated (or ethylated or propylated) PIP-T is introduced into and homogeneously dispersed into a natural or synthetic resinous material which is to be stabilized. By "by essentially pure" we refer to a hindered amine light stabilizer (HALS) which is at least 95% pure and has less than 500 ppm (parts per million) ash, preferably less than 100 ppm being the oxides of metal impurities which are critical in determining degradation of color. By "stabilization effect" we refer specifically to the effect on the material which must be protected against degradation by heat and light, especially ultraviolet (UV) light. For polyacetal compositions containing the methylated (or ethylated or propylated) PIP-T, such an effect can be determined by testing the discoloration and weight loss that occurs, if any does occur, in such compositions upon exposure to ultraviolet light and by further testing the thermal stability of such compositions.

Because the PSP is to be connected to the triazine ring through the N atom of the amine group in the bridge, thus forming the PIP-T, the PSP must necessarily be unsubstituted at the $N^4$ atom before making the connection. The obvious reason is that any substitution made at the $N^4$ atom before connecting the PSP to the triazine ring, would also be made at the N atom of the amino group, thus frustrating the connection to the triazine ring.

Since the function of the substituents on the ring and the bridge are now found to be clearly related to the effectiveness of the PIP-T as a stabilizer, it became imperative that any substitution of the $N^4$ atom be made after the connection of the PSP to the triazine ring.

The problem of alkylating the hindered $N^4$ atom in a diazacycloalkane molecule was solved in a straightforward manner in U.S. Pat. No. 4,190,571 in which a method of propylating the $N^4$ atom is disclosed. The 3,3,5,5-tetramethyl substituted diazepin-2-one was heated with 1-chloropropane. Thus, it was known that in a 3,3,5,5-tetramethyl substituted diazacycloalkane ring, the $N^4$ atom was not so highly hindered as to preclude "fitting" a propyl group into the space defined by the adjacent substituents on the 3- and 5-C atoms. As one would expect, having three polysubstituted diazacyclohexane groups attached to a single triazine ring would increase the difficulty of "finding" the $N^4$ atom. But connecting the PSPs to the triazine ring through the terminal primary amine group of the bridge would not be permitted because the H atom on the amine N atom connecting the PSP to the triazine ring, would also be methylated (or ethylated or propylated).

The problem of methylating a hindered N atom in a heterocyclic nitrogen compound has been addressed in a 2,2,6,6-tetrasubstituted piperidyl compound connected to plural triazine rings in U.S. Pat. No. 4,816,507 to Cantatore, et al. (Class 524/sub 100). Each triazine ring, in turn, is directly connected to the N atom of an acyclic polyamine and only two polysubstituted piperidyl substituents can be connected to each triazine ring. Further, each polysubstituted piperidyl substituent is directly connected to the triazine ring through a single tertiary N atom.

The difficulty of producing the methylated compound of the '507 patent is learned by carrying out the Eschweiler-Clark synthesis procedure described in Example 1 thereof. When the piperidyltriazine compound is methylated, a mixture of methylated compounds results. The major amount is a compound containing 8 pentamethylated piperidyl groups, and a 9th methyl group on either the terminal $N^I$ or $N^{IV}$ atoms, and lesser amounts of compounds are formed in which neither terminal and atom or both of them are methylated. There is no suggestion of how the methylated compounds with the pentamethylated groups might be separated from unreacted starting material and other compounds in the reaction mass, and we know of no way to do so.

Though the degree of difficulty involved in making a substitution is not a criterion for unobviousness unless the compound cannot be made, the degree of difficulty becomes of critical importance if a mass of essentially pure crystals are to be made and there is no known method for making it. In the specific instance of the methylated PIP-T, if the compound recovered is less than 90% pure, the impurities and by-products of the reaction function as prodegradants in the resin substrate to be stabilized. Further, if the conversion to the methylated PIP-T is less than 90%, purification of the methylated PIP-T in the mixture is impractical.

PSPs have been substituted at the $N^4$ position in Japan Public Patent Disclosure Bulletin No. JP 63-8711 but there is no indication of how substitutions may have been made, nor how a mass of such $N^4$-substituted compound was recovered from the reaction mass.

This invention is specifically directed to the alkylated PIP-T in which each of the three $N^4$ atoms of each PSP are necessarily alkylated, said alkylation being done with a methyl group, an ethyl group, or a propyl group, and each N atom connecting the PSP to the triazine ring is the terminal tertiary N atom of an ethyleneamine bridge; to a stabilizer product which is an essentially pure mass of the PIP-T alkylated with a methyl group, an ethyl group, or a propyl group; and, to a process of making the product with a conversion of at least 90% by weight of the starting PIP-T.

SUMMARY OF THE INVENTION

It has been discovered that a known oxo-piperazinyl triazine compound in which a triazine ring is substituted at each of its three C atoms with a polysubstituted piperazine-2-one ("PSP") moiety distally spaced from the triazine ring by a polyalkyleneamine bridge (which compound is referred to as "the PIP-T" for brevity), can be alkylated at only the $N^4$ position provided the N atom of the bridge is a tertiary N atom and provided alkylation is done with a methyl group, an ethyl group, or a propyl group, preferably with a methyl group.

It is therefore a specific object of this invention to provide the alkylated PIP-T represented by the following structure

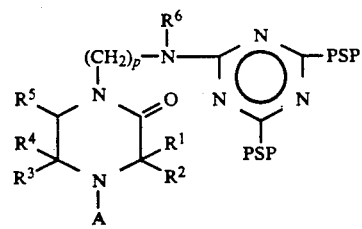

where

PSP represents the substituent with the structure shown;

A represents an alkyl group selected from methyl, ethyl, and propyl;

$R^1$, $R^2$, $R^3$, and $R^4$ each independently represent $C_1$-$C_6$ alkyl, or, when together cyclized, $R^1$ and $R^2$, and $R^3$ with $R^4$, represent $C_5$-$C_7$ cycloalkyl;

$R^5$ represents $C_1$-$C_6$ alkyl; $C_5$-$C_7$ cycloalkyl; $C_7$-$C_{12}$ aralkyl; hydrogen and phenyl;

$R^6$ represents $C_1$-$C_{12}$ alkyl and $C_5$-$C_{12}$ cycloalkyl; and p represents an integer in the range from 2 to about 12.

It has also been discovered that a mass of essentially pure crystals of the PIP-T used in an amount in the range from about 0.5 to 5 wt % based upon the total weight of the polyacetal and the HALS, is unexpectedly effective to stabilize the degradation of a polyacetal composition or an arbitrarily shaped thermoformed polyacetal article to thermal and oxidative degradation by heat and UV light.

It is therefore a specific object of this invention to provide a process for obtaining a mass of crystals of (VI) by alkylating each $N^4$ atom of each PSP in the known PIP-T using a process which unexpectedly provides at least 90% conversion to the alkylated PIP-T in a reaction mass from which the alkylated PIP-T is recovered as essentially pure (at least 90% pure) crystals, provided that said alkylation is done with a methyl group, an ethyl group, or a propyl group, and preferably, with a methyl group.

It is another specific object of this invention to provide a process for producing a mass of essentially pure crystals of (VI) from readily available compounds comprising, (a) reacting ethylenediamine with an aliphatic or cycloaliphatic aldehyde, and a nitroalkane or nitrocycloalkane at a temperature in the range from about ambient temperature (20° to about 60° C.), and pressure in the range from atmospheric to superatmospheric pressure up to about 100 psig to produce a reaction mixture containing a nitroamine (I); (b) without separating the reaction mixture, contacting the reaction mixture with molecular hydrogen at a pressure in the range from about 100 psig to about 1000 psig at a temperature in the range from about ambient temperature to about 120° C. in the presence of a Group VIII metal catalyst to produce a triamine (II); (c) reductively alkylating the triamine at only the terminal primary amine group of the ethyleneamine moiety to provide a N-substituted-N'-substituted-1,2-ethanediamine (III); (d) subjecting (III) to a ketoform reaction to produce a $N^1$-substituted PSP (IV); (e) reacting cyanuric chloride with at least 3 moles of (IV) to produce the PIP-T (V); (f) reacting a solution of (V) in an aromatic solvent in the presence of an excess of formic acid and formaldehyde to produce methylated PIP-T; and, (g) recovering essentially pure crystals of the PIP-T from the reaction mass.

DETAILED DESCRIPTION OF PREFERRED EMBODIMENTS

The structure of the known unmethylated PIP-T is represented as follows:

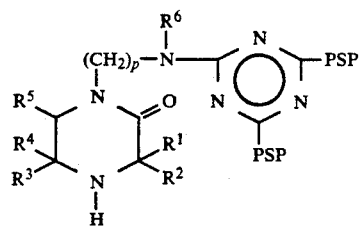
(V)

where PSP represents the substituent with the given structure; and, p, $R^1$, $R^2$, $R^3$, $R^4$, $R^5$, and $R^6$ have the same connotation as hereinbefore.

When a mass of essentially pure crystals of the PIP-T alkylated with a methyl group, an ethyl group, or a propyl group, in the aforementioned weight range, is used in polyacetal compositions, such compositions are stabilized more effectively than with either the unmethylated PIP-T or other known methylated piperidyltriazine compounds.

Because it is essential to provide the connecting bridge, the starting materials for preparing the PIP-T are an alkylenediamine, an aldehyde $R^5$CHO, and an appropriately substituted nitroalkane or nitrocycloalkane. As will be evident, the $R^5$ substituent is preserved on the 6- C atom of the PSP to be formed. Typically no substituent at the 6- C atom is provided, because formaldehyde or paraformaldehyde are used. To provide dimethyl substituents on the 3- C atom of the PSP, the starting nitroalkane is 2-nitropropane; and to provide a cyclohexyl group at the 3- C atom, nitrocyclohexane is used.

Particular starting materials are; ethylenediamine, formaldehyde, nitropropane; the triamine formed is reductively alkylated with cyclohexanone. The ketoform reaction is carried out with chloroform and acetone as reactants. Essentially pure crystals are produced with a conversion of at least 90% and recovered in a purity of at least 90%, and upon recrystallization are obtained with a purity of at least 95%. It is this material which is used as the stabilizer in the test conducted with polyacetal.

Thus, in the preparation of a 3,3,5,5,6-pentasubstituted piperazinone substituent for the PIP-T with the desired $N^4$ substituent to provide the bridge, the first step is the preparation of a triamine with terminal primary amine groups. Since an ethyleneamine bridge is generally adequate, the first step is as follows:

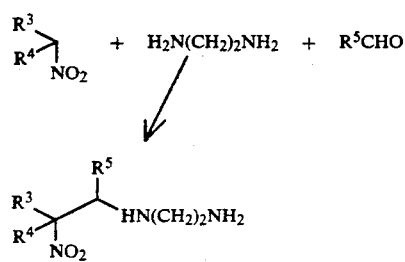
(I)

namely, N-(2-nitro-disubstituted)-1,2-ethanediamine, which is hydrogenated over Raney Ni to yield

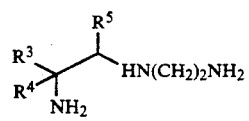
(II)

When starting with ethylenediamine, 2-nitropropane and paraformaldehyde the compound obtained is N-(2-methyl1-2-nitropropyl)-1,2-ethanediamine which when hydrogenated yields N-(2-amino-2-methylpropyl)-1,2-propanediamine

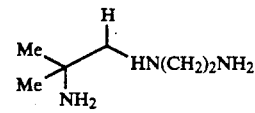

This triamine with terminal primary amine groups is then reductively alkylated with a ketone, for example cyclohexanone to yield N-cyclohexyl-N'-(2-amino-2-methylpropyl)-1,2-ethane-diamine

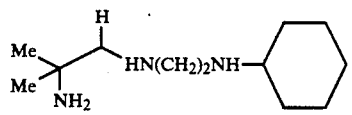
(III)

This N-substituted 1,2-ethanediamine is subjected to a ketoform reaction using the appropriate ketone to provide the desired $R^2$ and $R^3$ substituents on the PSP in structure (VI), and chloroform in the presence of sodium hydroxide or potassium hydroxide to produce the PSP substituent. To provide dimethyl substituents on the 3- C atom, acetone is used. The illustrative PSP formed is represented as

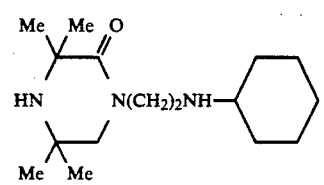
(IV)

Me = methyl

This PSP, or other PSP with the desired substituents on the ring, is then reacted with cyanuric chloride to yield the PIP-T having the general structure (V) and the specific structure (VII)

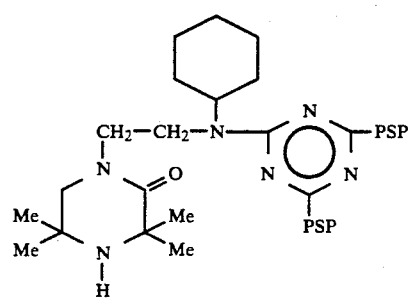
(VII)

PIP-T (VII) is alkylated with a methyl group, an ethyl group, or a propyl group at each N⁴ atom of each PSP in the PIP-T using a process which unexpectedly provides at least 90% conversion of the alkylated PIP-T in a reaction mass from which the alkylated PIP-T is recovered as essentially pure (at least 90% pure) crystals, as described herebelow. Essentially pure crystals are produced with a conversion of at least 90% and recovered in a purity of at least 90%, and upon recrystallization are obtained with a purity of at least 95%. It is this material which is at least 95% pure.

The alkylated PIP-T (VII) is dissolved in toluene and reacted with from about a 5% to about 10% molar excess of the stoichiometrically required amount of paraformaldehyde and formic acid. The reaction proceeds under reflux conditions for from about 2 to 5 hr after which the reaction mass is neutralized with aqueous ammonium hydroxide. The organic layer is washed with water and toluene is stripped from the water-washed layer to leave a concentrated solution of the alkylated PIP-T and other organic reaction products in toluene. Upon addition of heptane to the concentrated solution, the alkylated PIP-T is precipitated from solution, and recovered by filtration.

EXAMPLES

The following are the results of tests conducted with polyacetal compositions to determine the effectiveness of the stabilization provided by the methylated PIP-T, its unmethylated PIP-T (VII) precursor, and a methylated piperidyl-triazine compound, each of which is generically referred to as a HALS (hindered amine light stabilizer) in the data tables that follow. All temperatures are in °C. unless otherwise specified. Measurements are rounded where appropriate.

The polyacetal polymer (PAc) used in the examples below was an acetate end-capped homopolymer having a number average molecular weight of about 40,000.

In the following Tables comparisons have been made to determine the measurable effects of incorporating each of the preceding HALS with a blank (polyacetal containing no HALS, the blank designated 100 wt % PAc) and each of the various test samples contains a single HALS designated by the following codes and having the purity stated:

| Code | Identif. | Purity % | m. pt., °C. | ash, ppm |
|------|----------|----------|-------------|----------|
| C1 | PIP-T(K) | 97.5 | 175.5–178.5 | 100 |
| C2 | PIP-T(N) | 98 | not measured | 30 |
| C3 | PIP-T(R) | 99.2 | 181–182 | 10 |
| C4 | methylated piperdyl-triazine | | 154–160 | 400 |
| A | methylated PIP-T | 98 | 170–180 | 50 |

"C4" has the following structure:

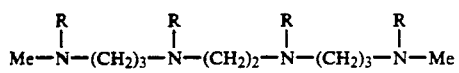

where Me=methyl

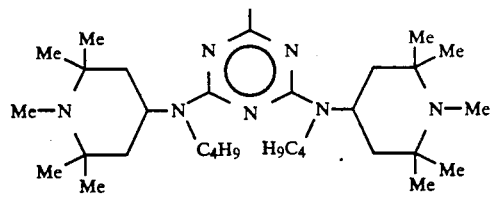

The thermal stability of the compositions tested was determined using a test procedure in which formaldehyde evolved upon thermal degradation of the PAc ('thermally evolved formaldehyde') is measured. A weighed sample of the polyacetal composition to be tested was placed in a tube and the tube was fitted with a cap for introduction of nitrogen to the test sample for removal of any evolved gases from the apparatus while maintaining the sample in an oxygen-free environment. The tube that contained the sample was heated at either 250° C., or at 259° C. in a silicone oil bath. The nitrogen and any evolved gases transported thereby were bubbled through 75 ml of a 40 g/liter sodium sulfite in water solution. Any evolved formaldehyde reacts with the sodium sulfite to liberate sodium hydroxide. The sodium hydroxide was continuously neutralized with standard 0.1N HCl. The results were obtained as a chart of ml of titer versus test time. The percent evolved formaldehyde was calculated by the formula $$(V)(N) \frac{(0.03 \times 100)}{SW}$$

where
V—the volume of titer in milliliters
N—the normality of the titer, and
SW—the sample weight in grams.

The factor "0.03" is the milliequivalent weight of formaldehyde in g/milliequivalent. Thermally evolved formaldehyde results are conveniently reported after fifteen minutes and after 30 min heating. The results are reported in the tables below under "Wt % CH₂O @×°C.".

EXAMPLES 1–2

Effect of Alkylated PIP-T on Polyacetal Fluff

The components of Examples 1 and 2 and comparison examples 1a, b and c; 2a, b and c; are listed below in Table I. For each example, a powdered HALS was added to polyacetal fluff, shaken to mix, and tested for thermally evolved formaldehyde (CH₂O), as described above. The results are reported in Table I below. The least degradation is seen with PIP-T(N) with 30 ppm ash (sample 1b), but its color is not as good as with "A" (methylated PIP-T, sample 1) at both concentrations. At the higher concentration (1% A) the weight per cent loss is greater than with PIP-T(R), namely sample 2c, but the color with A is much better. This resistance to degradation of color is particularly desirable with unpigmented and pigmented polyacetal, specially with pastels colors.

TABLE I

| Ex. No. | Wt. % PAc | Wt. % HALS | Wt. % CH₂O @ 250° C. 15 Min. | 30 Min. | Appearance after 30 min |
|---------|-----------|------------|-------|---------|-------------------------|
| Blank | 100 | — | 0.24 | 1.49 | White |
| 1 | 99.5 | 0.5 A | 0.58 | 2.34 | White |
| 1a | 99.5 | 0.5 C1 | 0.78 | 3.01 | Tan |

TABLE I-continued

| Ex. No. | Wt. % PAc | Wt. % HALS | Wt. % CH$_2$O @ 250° C. 15 Min. | 30 Min. | Appearance after 30 min |
|---|---|---|---|---|---|
| 1b | 99.5 | 0.5 C2 | 0.42 | 1.75 | Off-white/brown |
| 1c | 99.5 | 0.5 C3 | 0.57 | 2.33 | Off-white/brown |
| 2 | 99.0 | 1.0 A | 0.72 | 2.48 | White |
| 2a | 99.0 | 1.0 C1 | 0.90 | 2.68 | Dark Tan |
| 2b | 99.0 | 1.0 C2 | 0.63 | 2.16 | Brown |
| 2c | 99.0 | 1.0 C3 | 0.58 | 2.26 | Off-White/brown |

PAc - Polyacetal
HALS - Hindered Amine Light Stabilizer

EXAMPLES 3–4

Effect of Methylated PIP-T on Polyacetal (Melt Processed)

The components of Examples 3–4 and the related comparative examples 3a, 3b, 4a, 4b are listed below in Tables IIA and IIB. The samples were prepared as follows: the components were mixed together and melt compounded on a 28 mm Werner and Pfleiderer twin screw extruder with barrel temperature settings of 150° C. to 180° C., die temperature settings of 200° C., and screw speeds of 150 rpm. The temperature of the melt leaving the die ranged from 210° C. to 220° C.

The samples were tested for thermally evolved formaldehyde, described above. The samples were also tested to determine weight loss after UV exposure. Samples for the weight loss after UV exposure were molded plaques having dimensions of 5 cm×8.1 cm×4 mm. The molded plaques weighed between 21.9 to 22.5 grams and were provided with a textured surface finish resembling automotive vinyl. The textured side of the plaque was exposed to a UV light source for a predetermined exposure (i.e., 100, 200, or 300 kJ/m$^2$, as specified in Table IIB, below). All samples were subjected to UV exposure in the same apparatus, operated under the same conditions. Samples from each example were run simultaneously to eliminate test variation errors. Samples were weighed prior to testing. The samples were all subjected to accelerated UV exposure in an Atlas Ci65 Xenon Arc Weather-O-Meter operated as per SAE J1885 (Automotive Interior Conditions), with a quartz inner filter and a borosilicate outer filter. Pertinent details of the SAE J1885 method appear directly below as follows:

|  | Light Cycle | Dark Cycle |
|---|---|---|
| Irradiance (Watts/m$^2$) | 0.55 | — |
| Black Panel Temp (°C.) | 89 | 38 |
| Relative Humidity (%) | 50 | 100 |
| Cycle Time (hours) | 3.8 | 1.0 |

The calculation of sample exposure in terms of irradiation is as follows:

$$0.55\ W/m^2 = 0.55\ J/(m^2 \times sec)$$

$$0.55 \times 10^{-3}\ kJ/(m^2 \times sec) \times (3600\ s)/(1\ \text{light hour}) = 1.98\ kJ/m^2\ \text{per light hour}$$

where W=watt, m$^2$=meter squared, J=Joule, kJ=kilojoule.

Weight loss, a standard test for studying polyacetal UV degradation, is measured after UV exposure at the indicated amount detailed in Table IIB below by weighing the sample before and after exposure to UV light and then calculating wt % loss by the following formula:

$$(\text{unexp. wt}) - (\text{exp. wt})/(\text{unexp. wt}) \times 100\%$$

The data reported in Table IIA below shows that the methylated PIP-T of the present invention (Examples 3 and 4) has less of a degradative effect on the thermal stability of polyacetal than does the unmethylated PIP-T compound (3a and 4a). At the 1% loading level, methylated PIP-T (ex 4a) has less of a degradation effect on tensile strength of polyacetal than does 4b.

TABLE IIA

|  |  |  | Wt % CH$_2$O @ 259° C. | |
|---|---|---|---|---|
| Ex. No. | Wt % PAc | Wt % HALS | 15 Min. | 30 Min. |
| Blank | 100 | — | 1.07 | 2.57 |
| 3 | 99.5 | 0.5 A | 1.13 | 3.24 |
| 3a | 99.5 | 0.5 C1 | 1.59 | 5.90 |
| 3b | 99.5 | 0.5 C4 | 1.14 | 3.01 |
| 4 | 99.0 | 1.0 A | 0.61 | 2.60 |
| 4a | 99.0 | 1.0 C1 | 2.03 | 6.56 |
| 4b | 99.0 | 1.0 C4 | 1.72 | 3.65 |

PAc - Polyacetal
HALS - Hindered Amine Light Stabilizer

From the following data in Table IIB it is seen that the weight loss after exposure to 100 kJ/m$^2$ is least for samples 3 and 4 whether at 0.5 or 1 wt %. This is still true at 200 and 300 kJ/m$^2$. The surface appearance was best with A (methylated PIP-T) under all conditions.

TABLE IIB

| Ex. No. | Wt % PAc | Wt % HALS | % Wt Loss After Uv Exposure 100 kJ/m$^2$ | 200 kJ/m$^2$ | 300 kJ/m$^2$ | Appearance 100 kJ/m$^2$ | 200 kJ/m$^2$ | 300 kJ/m$^2$ |
|---|---|---|---|---|---|---|---|---|
| Blank | 100 | — | 0.61 | 1.56 | 4.31 | chalked | moderately chalked | heavily chalked |
| 3 | 99.5 | 0.5 A | 0.04 | 0.14 | 0.32 | — | — | I |
| 3a | 99.5 | 0.5 C1 | 0.07 | 0.18 | 0.36 | — | — | I, IV |
| 3b | 99.5 | 0.5 C4 | 0.10 | 0.19 | 0.77 | — | I, IV | III, IV |
| 4 | 99.0 | 1.0 A | 0.05 | 0.16 | 0.36 | — | — | I |
| 4a | 99.0 | 1.0 C1 | 0.09 | 0.35 | 1.71 | — | I, IV | III, IV |

TABLE IIB-continued

| Ex. No. | Wt % PAc | Wt % HALS | % Wt Loss After Uv Exposure ||| Appearance |||
| --- | --- | --- | --- | --- | --- | --- | --- | --- |
| | | | 100 kJ/m² | 200 kJ/m² | 300 kJ/m² | 100 kJ/m² | 200 kJ/m² | 300 kJ/m² |
| 4b | 99.0 | 1.0 C4 | 0.10 | 0.26 | 0.75 | — | IV | III, IV |

PAc - Polyacetal
HALS - Hindered Amine Light Stabilizer
Appearance Codes: plaques were examined using 7× magnification.
I - crazed - hairline cracking as a continuous line, no fissure evident.
II - lightly cracked, two sides of the crack separated by narrow fissure.
III - moderately cracked, cracks with fissures visible to the naked eye.
IV - edge cracking, cracks on edges of plaque clearly visible to the naked eye.

EXAMPLES 5-7

Effect of Methylated PIP-T on Polyacetal (Melt Processed)

The components of Examples 5-7 and comparative examples 5a-7a are listed below in Table III. The UV absorber A was a benzotriazole-type UV absorber. Additionally, the compositions each contained polyacetal A, 0.5% of a polyethylene-glycol lubricant, 0.13% of an antioxidant, 0.25% of a polyamide stabilizer, and 0.75% of a polyhydroxy polymer stabilizer. The sample compositions were prepared as follows: all components were mixed together and melt compounded on a two and one-half inch Sterling single screw extruder with barrel temperature settings ranging from 120° C. to 180° C., die temperature settings of 200° C., and screw speeds of 150 rpms. The temperature of the melt as it exited the die ranged from 210° C. to 220° C.

Samples were tested for thermally evolved formaldehyde, as described above. Samples were also subjected to air oven aging studies. For the air oven aging studies, the melt compounded samples were molded into ⅛-inch thick tensile bars. The tensile bars for each composition were preweighed and placed in a circulating air oven at 130° C. for the times noted in Table III, below. Oven location effects were averaged by distributing bars of a sample throughout the oven. At the end of the specified time period, the tensile bars were removed from the oven, weighed, and tested for tensile strength and elongation according to ASTM Method D-638 (0.2 in/min crosshead speed). The percent weight loss was calculated as [1−(weight after aging)/(weight before aging)]×100.

The results in Table III, below, show that weight loss after both 20 and 40 days is significantly less and physical properties are better retained for polyacetal compositions containing the methylated PIP-T compound (Examples 5, 6, 7) than for polyacetal compositions containing the methylated piperidyl triazine compound (Control Examples 5a, 6a, 7a).

What is claimed is:

1. The stabilizer compound

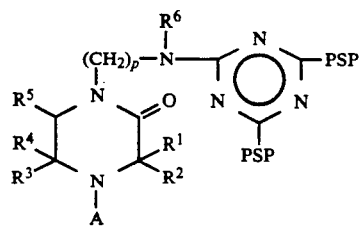

where
PSP represents a substituent on the triazine ring said substituent having the structure

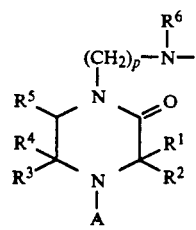

A represents $C_1-C_3$ alkyl;
$R^1$, $R^2$, $R^3$, and $R^4$ each independently represent $C_1-C_6$ alkyl, or, when together cyclized, $R^1$ with $R^2$, and $R^3$ with $R^4$, represents $C_5-C_7$ cycloalkyl;
$R^5$ represents $C_1-C_6$ alkyl; $C_5-C_7$ cycloalkyl; $C_7-C_{12}$ aralkyl; hydrogen and phenyl;
$R^6$ represents $C_1-C_{12}$ alkyl and $C_5-C_{12}$ cycloalkyl;
and, p represents an integer in the range from 2 to about 12.

2. The stabilizer compound of claim 1 wherein $R^1$, $R^2$, $R^3$, and $R^4$ are each methyl, and A is methyl.

3. The stabilizer compound of claim 2 having the structure

TABLE III

| Ex. No. | Wt % HALS | Wt % UV Absorber | Wt % CH₂O @259° C. || Air Oven Aging @ 130° C. ||||||
| --- | --- | --- | --- | --- | --- | --- | --- | --- | --- | --- |
| | | | | | 0 Days | 20 Days ||| 40 Days |||
| | | | 15 Min. | 30 Min. | % Elong | Tens Strg * | Wt Loss | % Elong | Tens Strg * | Wt Loss | % Elong | Tens Strg * |
| Blnk | — | — | 0.11 | 0.40 | 36.2 | 9.5 | 0.51 | 5.0 | 9.1 | 1.33 | 2.5 | 7.1 |
| 5 | 0.15 A | 0.15 | 0.12 | 0.44 | 53.3 | 8.9 | 0.49 | 17.9 | 10.4 | 1.06 | 2.7 | 6.6 |
| 5a | 0.15 C4 | 0.15 | 0.06 | 0.32 | 47.2 | 9.2 | 1.05 | 2.6 | 6.5 | 2.94 | 2.3 | 5.8 |
| 6 | 0.3 A | 0.3 | 0.07 | 0.44 | 33.3 | 9.2 | 0.33 | 18.8 | 10.4 | 1.03 | 2.3 | 6.8 |
| 6a | 0.3 C4 | 0.3 | 0.18 | 0.57 | 38.0 | 9.3 | 1.03 | 2.1 | 6.1 | 3.25 | 1.5 | 5.1 |
| 7 | 0.6 A | 0.6 | 0.15 | 0.54 | 32.1 | 9.2 | 0.56 | 19.1 | 10.4 | 1.00 | 1.9 | 6.3 |
| 7a | 0.6 C4 | 0.6 | 0.10 | 0.49 | 43.0 | 9.1 | 1.30 | 1.9 | 6.0 | 3.66 | 1.5 | 4.0 |

HALS = Hindered Amine Light Stabilizer
* = Kpsi

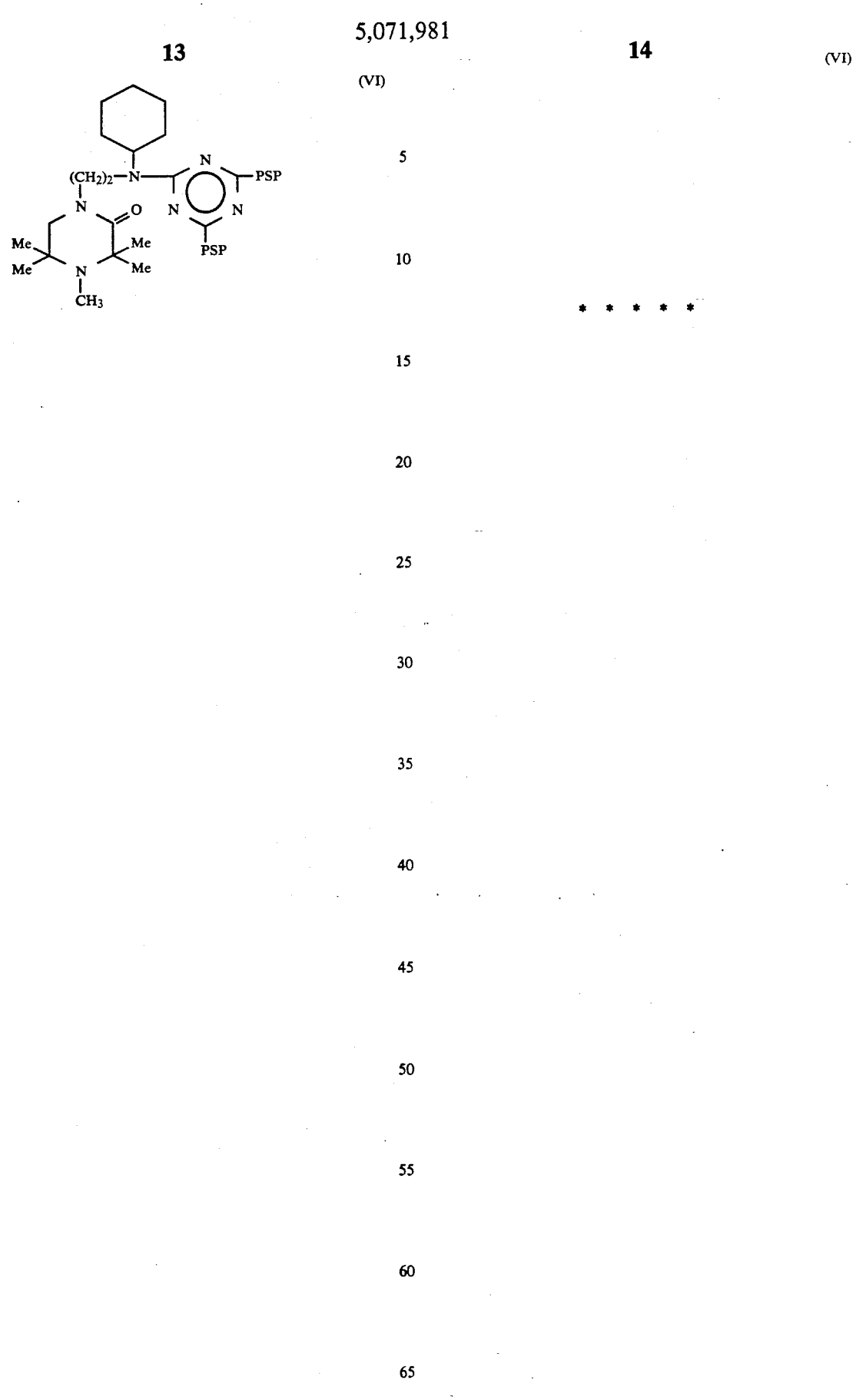
(VI)
* * * * *